United States Patent
DiNardo et al.

(10) Patent No.: US 12,396,728 B2
(45) Date of Patent: *Aug. 26, 2025

(54) STAPLE CARTRIDGE HAVING RETAINER MOVABLE BETWEEN CONFIGURATIONS

(71) Applicant: Cilag GmbH International, Zug (CH)

(72) Inventors: Brian F. DiNardo, Loveland, OH (US); Morgan R. Hunter, Cincinnati, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/614,111

(22) Filed: Mar. 22, 2024

(65) Prior Publication Data

US 2024/0341762 A1 Oct. 17, 2024

Related U.S. Application Data

(63) Continuation of application No. 17/969,220, filed on Oct. 19, 2022, now Pat. No. 11,963,680, which is a continuation of application No. 17/100,104, filed on Nov. 20, 2020, now Pat. No. 11,478,244, which is a continuation of application No. 15/798,876, filed on Oct. 31, 2017, now Pat. No. 10,842,490.

(51) Int. Cl.
*A61B 17/072* (2006.01)
*A61B 17/00* (2006.01)
*A61B 90/00* (2016.01)

(52) U.S. Cl.
CPC .............. *A61B 17/07207* (2013.01); *A61B 2017/00477* (2013.01); *A61B 2017/07257* (2013.01); *A61B 2017/07271* (2013.01); *A61B 2017/07278* (2013.01); *A61B 2090/0807* (2016.02); *A61B 2090/0814* (2016.02)

(58) Field of Classification Search
CPC ........... A61B 2017/00477; A61B 2017/07271; A61B 2090/0814; A61B 2090/0807; A61B 17/07207

See application file for complete search history.

(56) References Cited

U.S. PATENT DOCUMENTS

| | | | |
|---|---|---|---|
| 6,988,649 B2 * | 1/2006 | Shelton, IV | A61B 17/07207 227/176.1 |
| 9,072,535 B2 | 7/2015 | Shelton, IV et al. | |
| 9,492,146 B2 * | 11/2016 | Kostrzewski | A61B 17/29 |
| 9,668,734 B2 * | 6/2017 | Kostrzewski | A61B 17/07207 |
| 9,700,320 B2 * | 7/2017 | Dinardo | A61B 17/07207 |
| 9,808,244 B2 | 11/2017 | Leimbach et al. | |
| 10,792,038 B2 | 10/2020 | Becerra et al. | |
| 10,842,490 B2 | 11/2020 | DiNardo et al. | |

(Continued)

*Primary Examiner* — Andrew M Tecco

(57) ABSTRACT

A surgical instrument includes a sled and an end effector. The end effector includes a first jaw, a second jaw movable relative to the first jaw, an anvil, and a cartridge channel. The staple cartridge includes a proximal end, a distal end, a cartridge body, and staples supported in the cartridge body, wherein the sled is movable to deploy the staples from the cartridge body against tissue captured between the staple cartridge and the anvil. The cartridge channel is configured to removably retain the staple cartridge, wherein a load is required to remove the staple cartridge from the cartridge channel, and wherein the sled is configured to reduce the cartridge removal load.

20 Claims, 12 Drawing Sheets

(56) References Cited

U.S. PATENT DOCUMENTS

| | | | |
|---|---|---|---|
| 11,478,244 B2 | 10/2022 | DiNardo et al. | |
| 11,963,680 B2 | 4/2024 | DiNardo et al. | |
| 2004/0232200 A1* | 11/2004 | Shelton, IV | A61B 17/07207 227/176.1 |
| 2013/0274722 A1* | 10/2013 | Kostrzewski | A61B 17/29 606/1 |
| 2015/0327862 A1* | 11/2015 | Kostrzewski | A61B 17/07207 227/178.1 |
| 2016/0058440 A1* | 3/2016 | Dinardo | A61B 17/07207 227/176.1 |
| 2016/0374678 A1* | 12/2016 | Becerra | A61B 17/07207 227/177.1 |

* cited by examiner

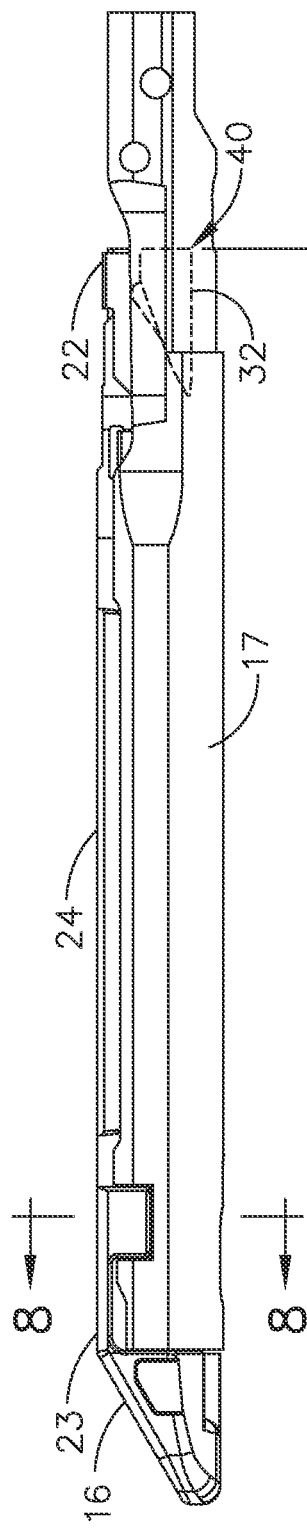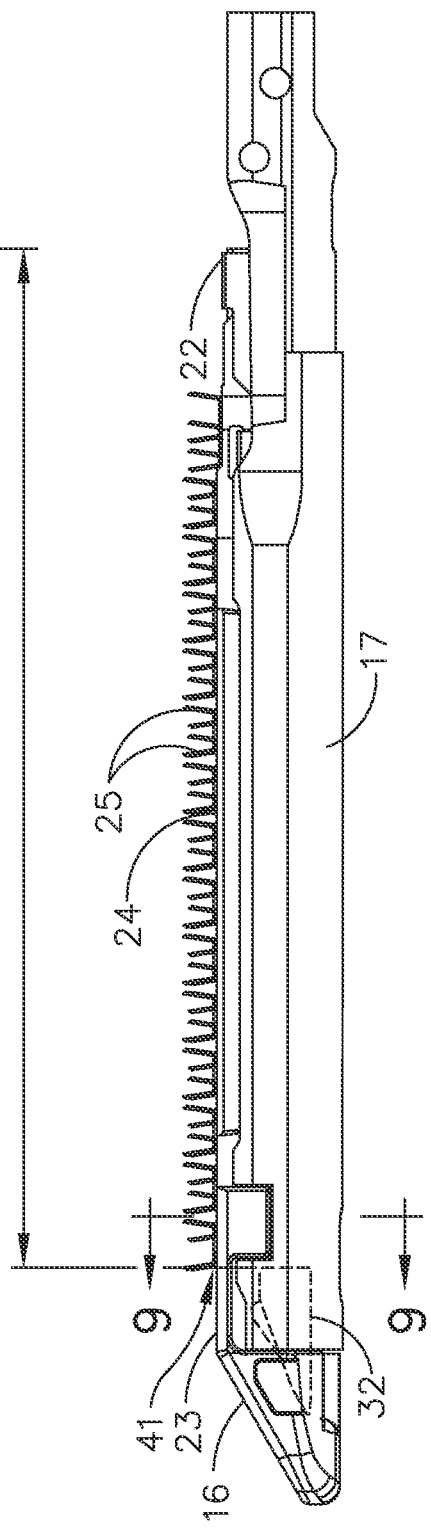
FIG. 6
FIG. 7

STAPLE CARTRIDGE HAVING RETAINER MOVABLE BETWEEN CONFIGURATIONS

CROSS-REFERENCE TO RELATED APPLICATIONS

This application is a continuation application claiming priority under 35 U.S.C. § 120 to U.S. patent application Ser. No. 17/969,220, entitled CARTRIDGE BODY DESIGN WITH FORCE REDUCTION BASED ON FIRING COMPLETION, filed Oct. 19, 2022, which issued on Apr. 23, 2024 as U.S. Pat. No. 11,963,680, which is a continuation application claiming priority under 35 U.S.C. § 120 to U.S. patent application Ser. No. 17/100,104, entitled CARTRIDGE BODY DESIGN WITH FORCE REDUCTION BASED ON FIRING COMPLETION, filed Nov. 20, 2020, which issued on Oct. 25, 2022 as U.S. Pat. No. 11,478,244, which is a continuation application claiming priority under 35 U.S.C. § 120 to U.S. patent application Ser. No. 15/798,876, entitled CARTRIDGE BODY DESIGN WITH FORCE REDUCTION BASED ON FIRING COMPLETION, filed Oct. 31, 2017, which issued on Nov. 24, 2020 as U.S. Pat. No. 10,842,490, the entire disclosures of which are hereby incorporated by reference herein.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 6 illustrates a staple cartridge assembled with a cartridge channel of the surgical instrument of FIG. 1 with a sled shown in phantom lines in a proximal position;

FIG. 7 illustrates a staple cartridge assembled with a cartridge channel of the surgical instrument of FIG. 1 with a sled shown in phantom lines in a distal position;

DETAILED DESCRIPTION

Figure 1:
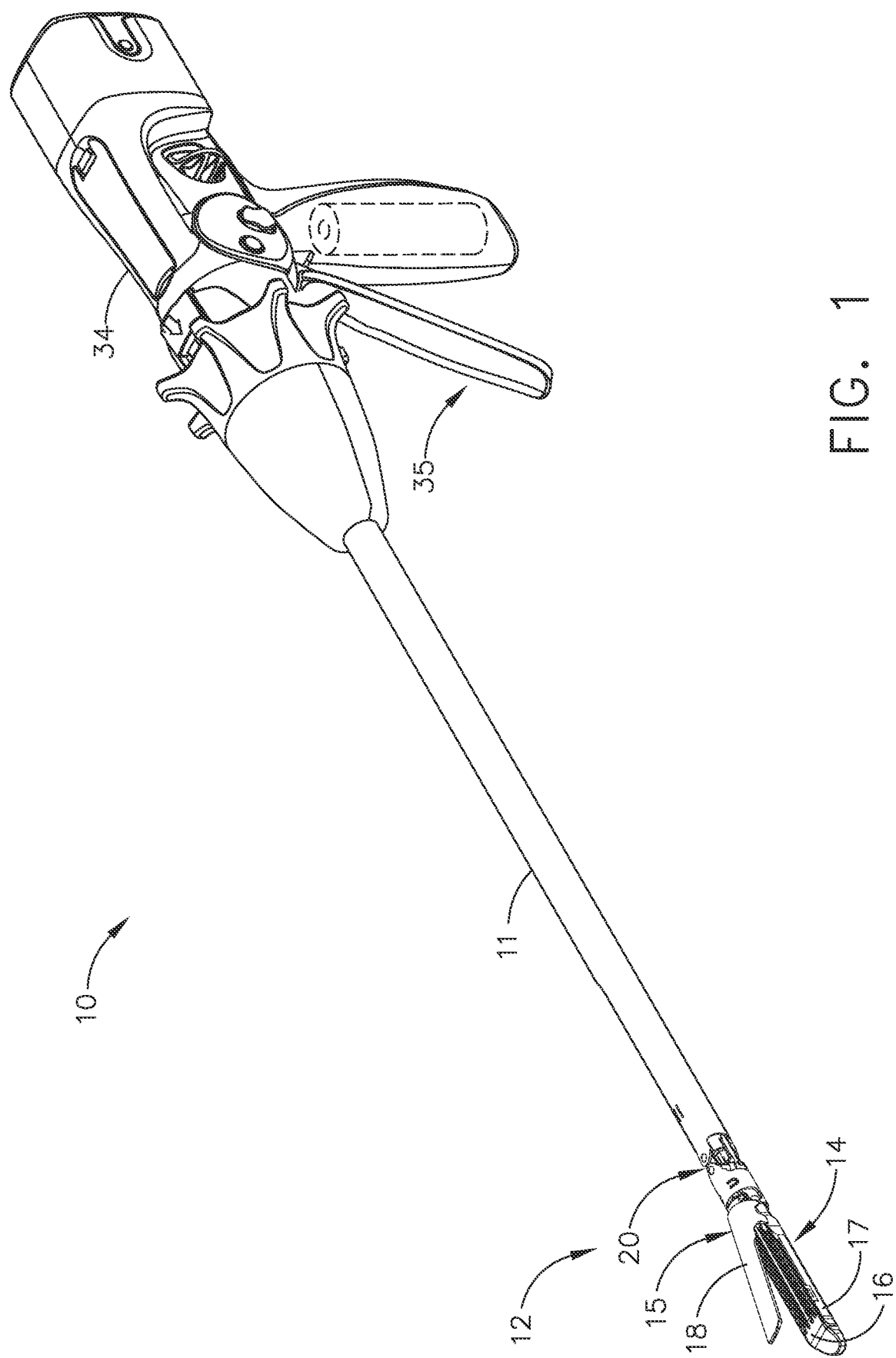
FIG. 1 illustrates perspective view of a surgical instrument in accordance with at least one aspect of the present disclosure.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Although various aspects of the present disclosure have been described herein in connection with linear staplers, these aspects can be similarly implemented in other surgical staplers such as, for example, circular staplers and/or curved staplers. Also although various aspects of the present disclosure are described in connection with a hand-held instrument, these aspects can be similarly implemented in robotic surgical systems. Various suitable robotic surgical systems are disclosed in U.S. Patent No. 2012/0298719, entitled SURGICAL STAPLING INSTRUMENTS WITH ROTATABLE STAPLE DEPLOYMENT ARRANGEMENTS, filed May 27, 2011, now U.S. Pat. No. 9,072,535, the entire disclosure of which is incorporated by reference herein.

Figure 2:
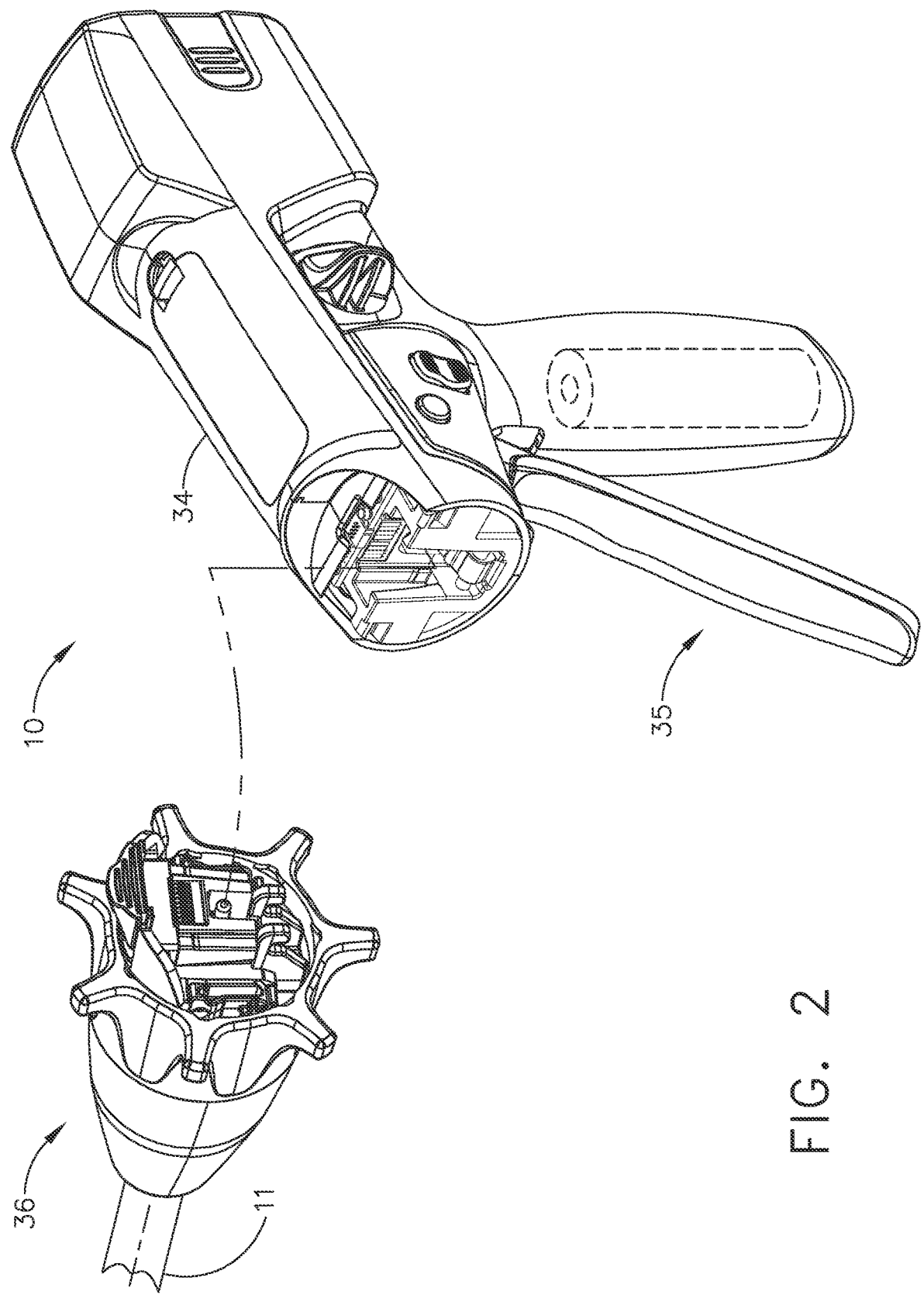
FIG. 2 illustrates is a partial perspective view of an interchangeable shaft assembly and a perspective view of a handle of the surgical instrument of FIG. 1 in an unassembled configuration.
Figure 3:
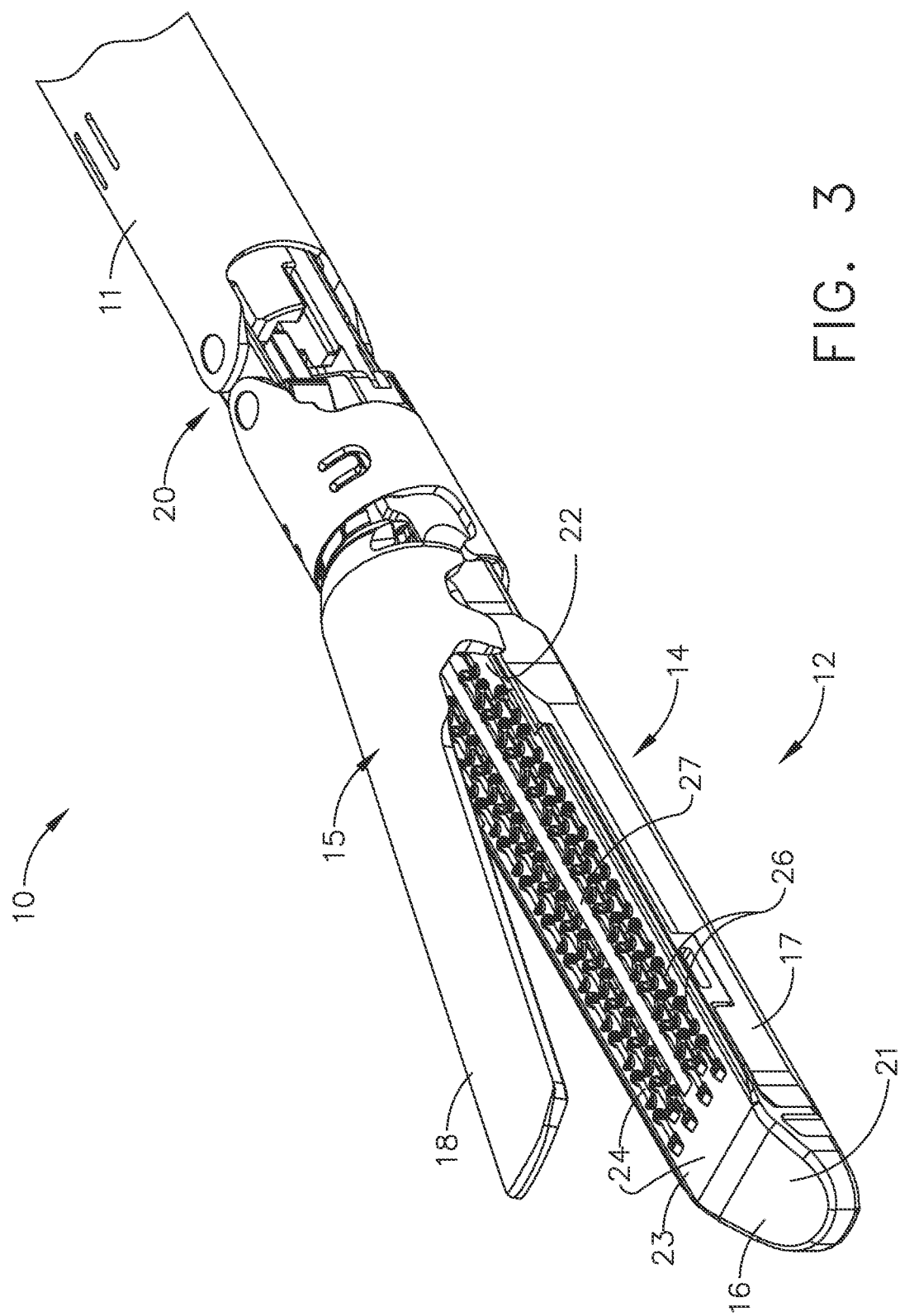
FIG. 3 illustrates perspective view of an end effector of the surgical instrument of FIG. 1.

Referring primarily to FIGS. 1-3, a surgical stapling instrument 10 comprises a shaft 11 and an end effector 12 extending from the shaft 11. The end effector 12 comprises a first jaw 14 and a second jaw 15. The first jaw 14 comprises a staple cartridge 16. The staple cartridge 16 is insertable into and removable from a cartridge pan or channel 17 of the first jaw 14; however, other embodiments are envisioned in which the staple cartridge 16 is not removable from, or at least readily replaceable from, the first jaw 14. The second jaw 15 comprises an anvil 18 configured to deform staples ejected from the staple cartridge 16. The second jaw 15 is pivotable relative to the first jaw 14 about a closure axis; however, other embodiments are envisioned in which the first jaw 14 is pivotable relative to the second jaw 15. The surgical stapling instrument 10 further comprises an articulation joint 20 configured to permit the end effector 12 to be rotated, or articulated, relative to the shaft 11. The end effector 12 is rotatable about an articulation axis extending through the articulation joint 20. Other embodiments are envisioned which do not include an articulation joint.

Referring to FIG. 2, in various examples, the surgical stapling instrument 10 includes a housing 34 that comprises a handle assembly 35 that is configured to be grasped, manipulated, and actuated by the clinician. The housing 34 is configured for operable attachment to an interchangeable shaft assembly 36, which includes the end effector 12 and at least a portion of the shaft 11. In accordance with the present disclosure, various forms of interchangeable shaft assemblies may be effectively employed in connection with robotically controlled surgical systems as well hand-held instruments. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a hand-held surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, entitled SURGICAL STAPLING INSTRUMENTS WITH ROTATABLE STAPLE DEPLOYMENT ARRANGEMENTS, which is herein incorporated by reference in its entirety.

Figure 4:
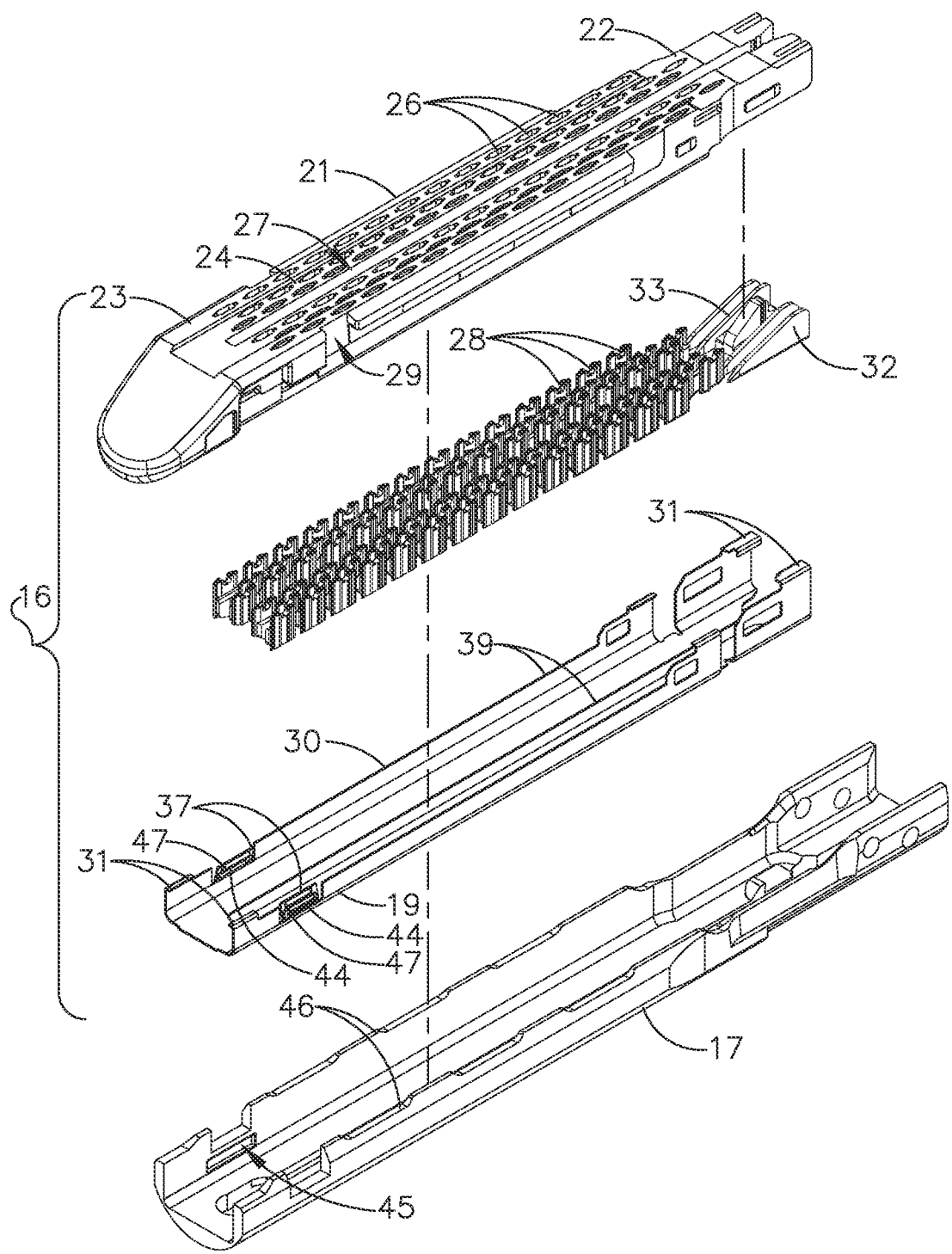
FIG. 4 illustrates an exploded view of a staple cartridge and a cartridge channel of the end effector of FIG. 3.

Referring primarily to FIGS. 3 and 4, the staple cartridge 16 comprises a cartridge body 21. The cartridge body 21 includes a proximal end 22, a distal end 23, and a deck 24 extending between the proximal end 22 and the distal end 23. In use, the staple cartridge 16 is positioned on a first side of the tissue to be stapled and the anvil 18 is positioned on a second side of the tissue. The anvil 18 is moved toward the staple cartridge 16 to compress and clamp the tissue against the deck 24. Thereafter, staples 25 (FIG. 7) removably stored in the cartridge body 21 can be deployed into the tissue. The cartridge body 21 includes staple cavities 26 defined therein wherein the staples 25 are removably stored in the staple cavities 26. The staple cavities 26 are generally arranged in six longitudinal rows. Three rows of the staple cavities 26 are positioned on a first side of a longitudinal slot 27 and three rows of the staple cavities 26 are positioned on a second side of the longitudinal slot 27. Other arrangements of the staple cavities 26 and the staples 25 may be possible.

The staples 25 are supported by staple drivers 28 in the cartridge body 21. The staple drivers 28 are movable between a first, or unfired position, and a second, or fired, position to eject the staples 25 from the staple cavities 26. The staple drivers 28 are retained in the cartridge body 21 by a pan or retainer 30 which extends around the bottom of the cartridge body 21 and includes resilient members 31 configured to grip the cartridge body 21 and hold the retainer 30 to the cartridge body 21. The staple drivers 28 are movable between their unfired positions and their fired positions by a sled 32. The sled 32 is movable between a proximal position 40 (FIG. 6) adjacent the proximal end 22 and a distal position 41 (FIG. 7) adjacent the distal end 23. The sled 32 comprises a plurality of ramped surfaces 33 configured to slide under the staple drivers 28 and lift the staple drivers 28, and the staples 25 supported thereon, toward the anvil 18.

Further to the above, the sled 32 is moved distally by a firing member (not shown). The firing member is configured to contact the sled 32 and push the sled 32 from the proximal position 40 (FIG. 6) adjacent the proximal end 22 toward the distal position 41 (FIG. 7) adjacent the distal end 23. The longitudinal slot 27 defined in the cartridge body 21 is configured to receive the firing member. The anvil 18 also includes a slot (not shown) configured to receive the firing member. The firing member further comprises a first cam which engages the first jaw 14 and a second cam which engages the second jaw 15. As the firing member is advanced distally, the first cam and the second cam can control the distance, or tissue gap, between the deck 24 of the staple cartridge 16 and the anvil 18. The firing member also comprises a knife configured to incise the tissue captured intermediate the staple cartridge 16 and the anvil 18.

To properly deploy the staples from the staple cartridge by a firing member, the staple cartridge must be properly retained in the cartridge channel. Accordingly, it is desirable for the staple cartridge to be tightly secured to the cartridge channel for successful firing. After the staple cartridge is fired, however, a user may struggle to remove a fired staple cartridge that is tightly secured to the cartridge channel. The present disclosure provides various mechanisms for ensuring a tight attachment between an unfired staple cartridge and the cartridge channel, wherein the tight attachment is loosened or reduced by the firing mechanism to facilitate removal of the fired staple cartridge. In various examples, the tight attachment is loosened or reduced at a final stage of the firing process. In various examples, the tight attachment is loosened or reduced during the firing of the most distal group of staples. In various examples, the attachment is loosened or reduced when the sled 32 is adjacent the distal end 23 of the staple cartridge 16.

In various examples, the staple cartridge 16 includes one or more retaining members that are configured to ensure a tight attachment between an unfired staple cartridge 16 and a cartridge channel 17. The retaining members can be moved, or otherwise modified, during the firing of the staple cartridge 16 to yield a reduced attachment between the fired staple cartridge 16 and the cartridge channel 17. The reduced attachment permits a user to easily remove the fired staple cartridge 16 from the cartridge channel 17.

Figure 5:
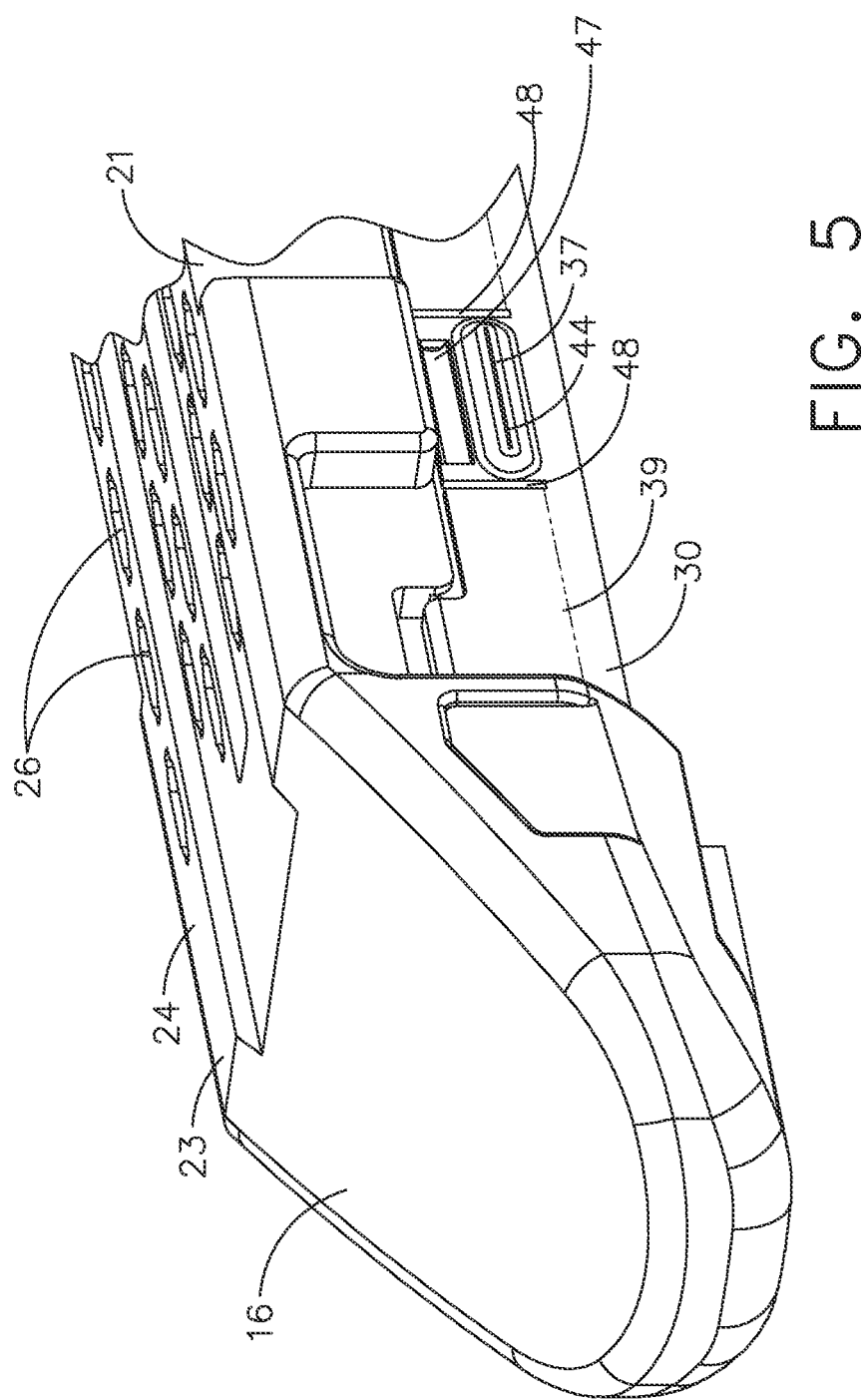
FIG. 5 illustrates a partial view of a staple cartridge of the surgical instrument of FIG. 1.

In the example illustrated in FIGS. 4 and 5, the staple cartridge 16 is removably seated in the cartridge channel 17. The staple cartridge 16 includes two retaining members 37 on opposite sides of the staple cartridge 16. The retaining members 37 are configured to maintain, or to help maintain, a tight attachment between the staple cartridge 16 and the cartridge channel 17. The retaining members 37 may extend from a base 19 of the retainer 30. In various examples, the retaining members 37 are spaced apart from walls 39 of the retainer 30 to permit the retaining members 37 to flex relative to the walls 39. In the example illustrated in FIG. 5, the retaining members 37 are separated from the walls 39 by slits 48.

Each retaining member 37 is in the form of a resilient member movable between a biased configuration (FIG. 8) in an unfired staple cartridge 16, and an unbiased, or less biased, configuration (FIG. 9) in a fired staple cartridge 16. In the unfired staple cartridge 16, the retaining member 37 is biased into an engagement with the cartridge channel 17 to maintain, or to help maintain, a pre-firing cartridge removal load. A load greater than or equal to the pre-firing cartridge removal load is needed to separate an unfired staple cartridge 16 from the cartridge channel 17.

In the fired staple cartridge 16, the engagement between the retaining member 37 is lessened, or eliminated, which yields a post-firing cartridge removal load that is less than the pre-firing cartridge removal load. The post-firing cartridge removal load permits a user to easily remove the fired staple cartridge 16 from the cartridge channel 17.

Figure 8:
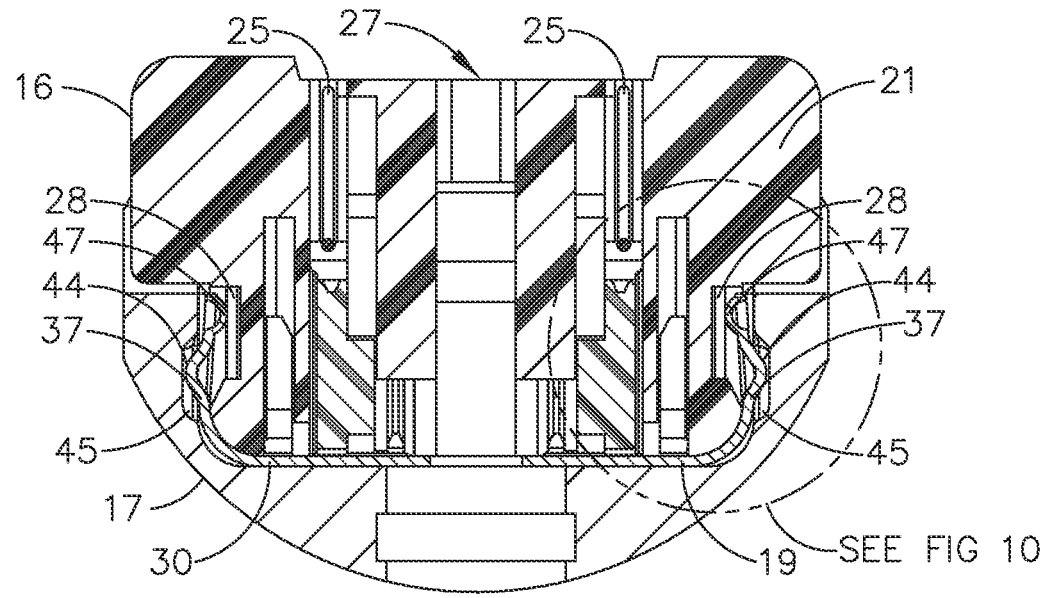
FIG. 8 illustrates a cross-sectional view taken along line 8-8 of FIG. 6.

Referring primarily to FIGS. 4 and 8, each retaining member 37 includes a first curved portion 44 that defines a first retention feature or detent receivable in a depression or groove 45 defined in a side wall 46 of the cartridge channel 17. The first curved portion 44 is retained in the groove 45 while the retaining member 37 is in the biased configuration. Each retaining member 37 further includes a second curved portion 47 that defines a second retention feature detent configured to rest against at least one staple driver 28 while the retaining member 37 is in the biased configuration. The cartridge body 21 includes a window 29 that exposes the at least one staple driver 28 to permit the second curved portion 47 to rest against the at least one staple driver 28. In various examples, each retaining member 37 defines a plane transecting the base 19, wherein the first curved portion 44 defines a first detent on the first side of the plane, and wherein the second curved portion 47 defines a second detent on the second side of the plane.

Figure 10:
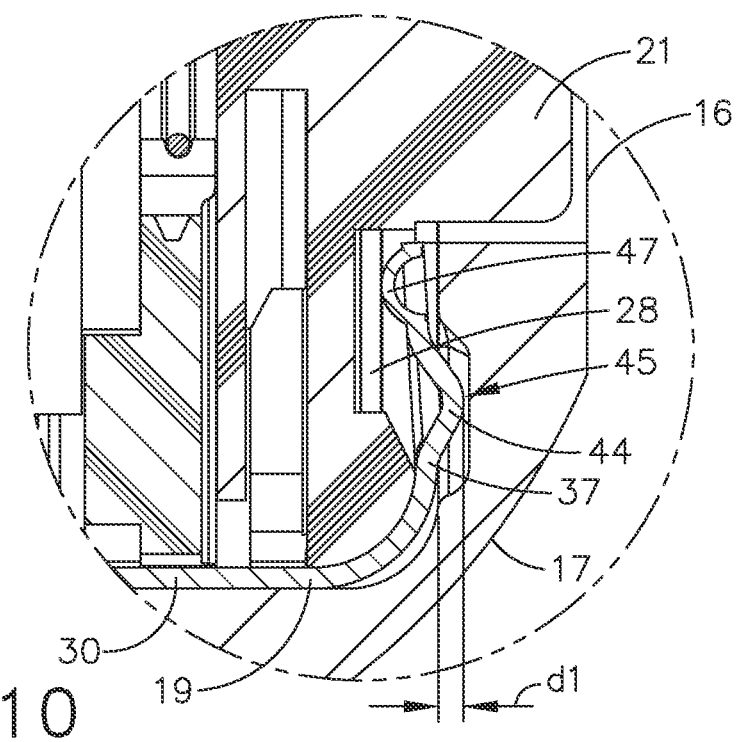
FIG. 10 illustrates a partial expanded view of the cross-sectional view of FIG. 8.

Prior to firing the staple cartridge 16 seated in the cartridge channel 17, as illustrated in FIGS. 8 and 10, the retaining member 37 is biased an interference distance (d1) by the at least one staple driver 28 toward the side wall 46, which causes the first curved portion 44 to be secured in the groove 45 yielding the pre-firing cartridge removal load.

Figure 9:
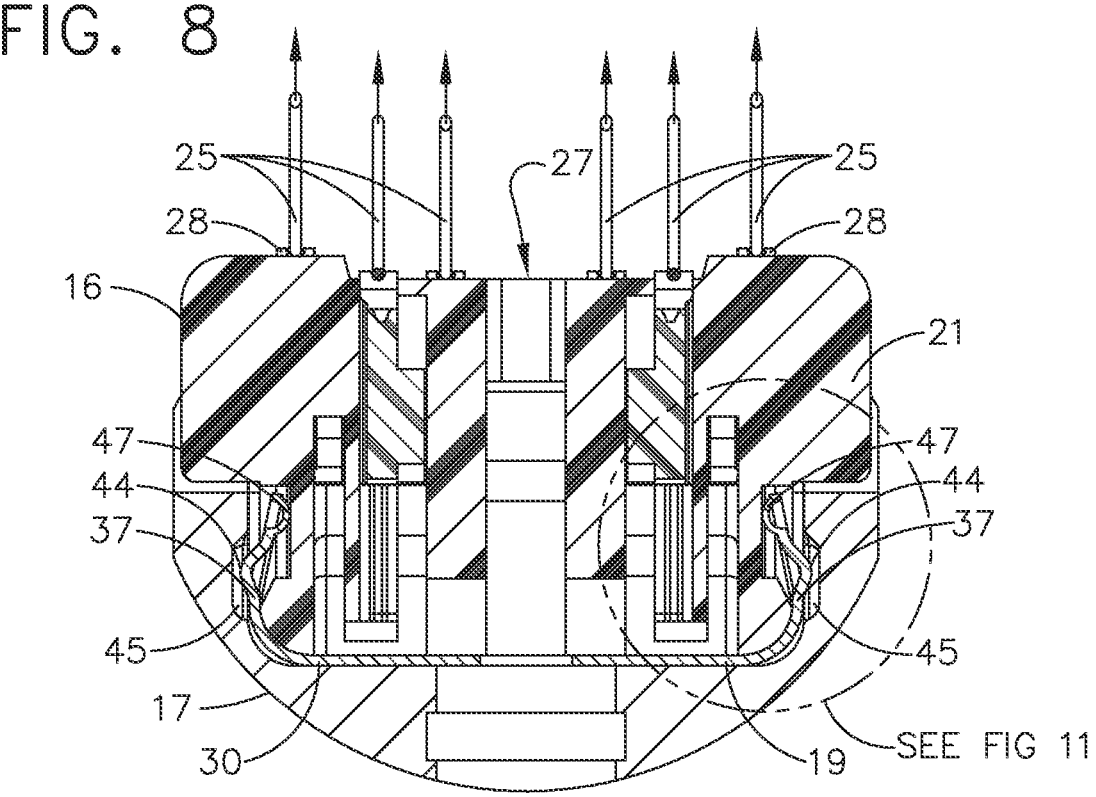
FIG. 9 illustrates a cross-sectional view taken along line 9-9 of FIG. 7.
Figure 11:
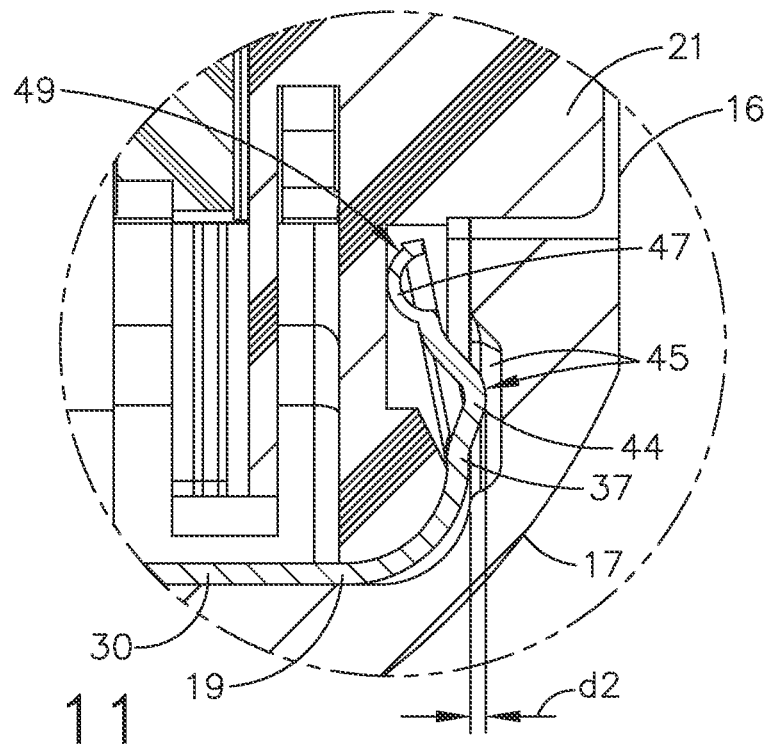
FIG. 11 illustrates a partial expanded view of the cross-sectional view of FIG. 9.

During firing, however, the sled 32 (FIG. 7) is advanced by the firing member causing the at least one staple driver 28 to be lifted or moved out of engagement, or at least partially out of engagement, with the retaining member 37. As illustrated in FIGS. 9 and 11, removal of the at least one staple driver 28 causes the retaining member 37 to return to the unbiased, or less biased, configuration, which causes the first curved portion 44 to fall out of engagement, or at least partially out of engagement, with the groove 45 yielding the post-firing cartridge removal load. As illustrated in FIG. 11, the retaining member 37 is biased an interference distance (d2) from a natural position, the interference distance (d2) being less than the interference distance (d1).

As described above, the sled 32 comprises a plurality of ramped surfaces 33 configured to slide under the staple drivers 28 and lift the staple drivers 28, and the staples 25 supported thereon, toward the anvil 18. As illustrated in FIGS. 10 and 11, the lifting of the at least one staple driver 28 by the sled 32 from a first position (FIG. 10) to a second position (FIG. 11), creates a gap 49 that is readily occupied by the retaining member 37 in the unbiased, or slightly biased, configuration.

In some examples, the first curved portion 44 remains partially inserted in the groove 45 in the unbiased configuration. Consequently, the retaining member 37 contributes to the post-firing cartridge removal load. In other examples, however, the first curved portion 44 may be fully removed from the groove 45 in the unbiased configuration. In the other examples, the retaining member 37 does not contribute to the post-firing cartridge removal load, which can be governed by the friction between the walls 39 of the staple cartridge 16 and the cartridge channel 17. In some examples, the first curved portion 44 of the retaining member 37 is replaced with two adjacent but separate curved portions that are received in two separate but adjacent grooves in the side wall 46 of the cartridge channel 17. In such examples, the two curved portions of the retaining member 37 are secured in the two grooves of the side wall 46 in the biased configuration yielding the pre-firing cartridge removal load. In the unbiased configuration, however, only one of the two curved portions remains secured in its groove yielding a post-firing cartridge removal load that is less than the pre-firing cartridge removal load. The examples of FIGS. 8-11 depict the retaining member 37 as a resilient member that yields the pre-firing cartridge removal load in a biased configuration and the lesser post-firing cartridge removal load in an unbiased, or less biased, configuration. In other examples, however, the retaining member 37 need not be a resilient member. In some examples, the retaining member 37 can be actively moved from the first position corresponding to the pre-firing cartridge removal load and the second position corresponding to the lesser post-firing cartridge removal load. In at least one example, the retaining member 37 can be configured to pivot between the first position and the second position about a pin. In the first position, the first curved portion 44 can be secured in the groove 45. The sled 32, or the firing member, can be configured to cause the retaining member 37 to move from the first position to the second position to cause the first curved portion 44 to fall out of engagement with the groove 45, for example.

Figure 12:
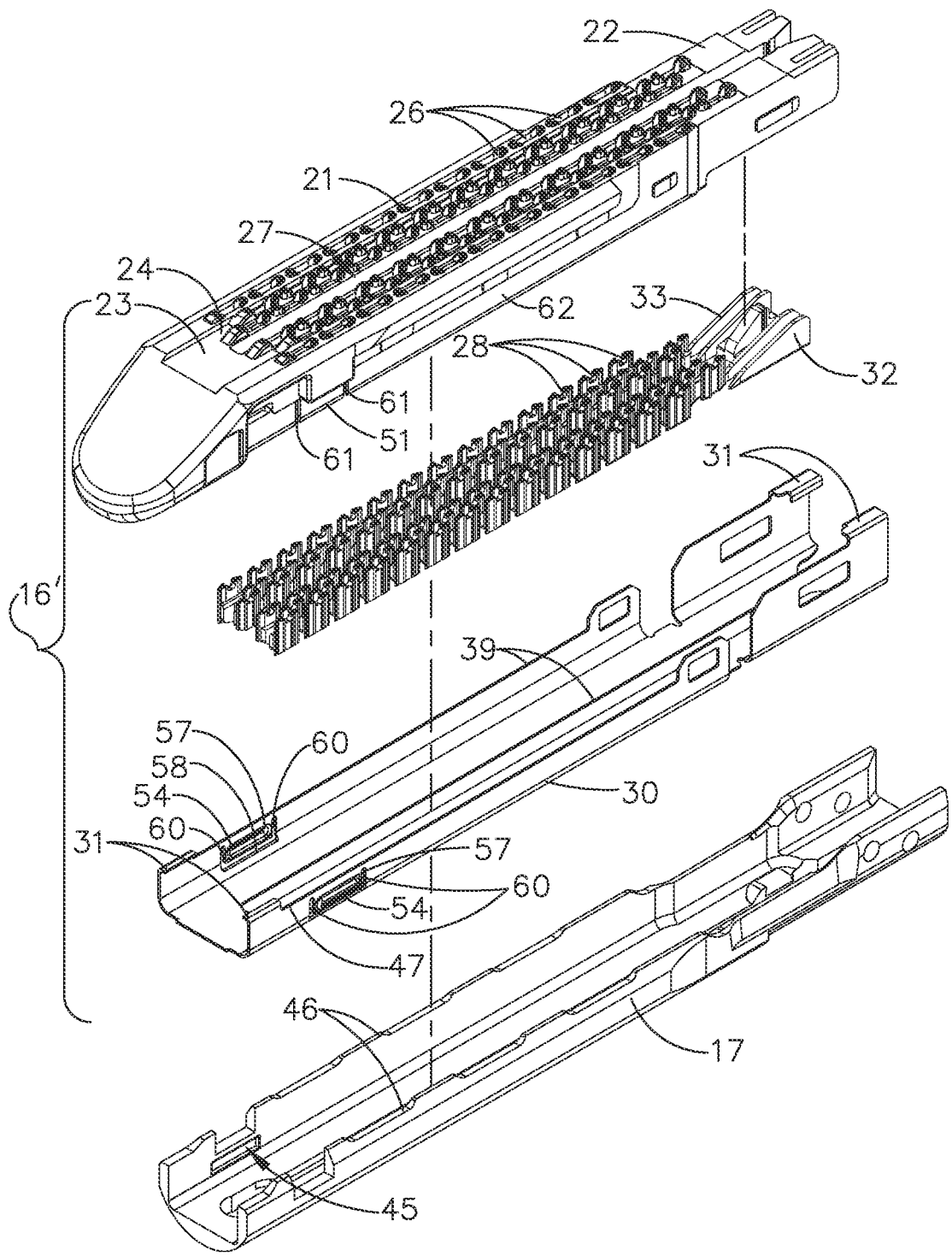
FIG. 12 illustrates an exploded view of a staple cartridge and a cartridge channel in accordance with at least one aspect of the present disclosure.
Figure 13:
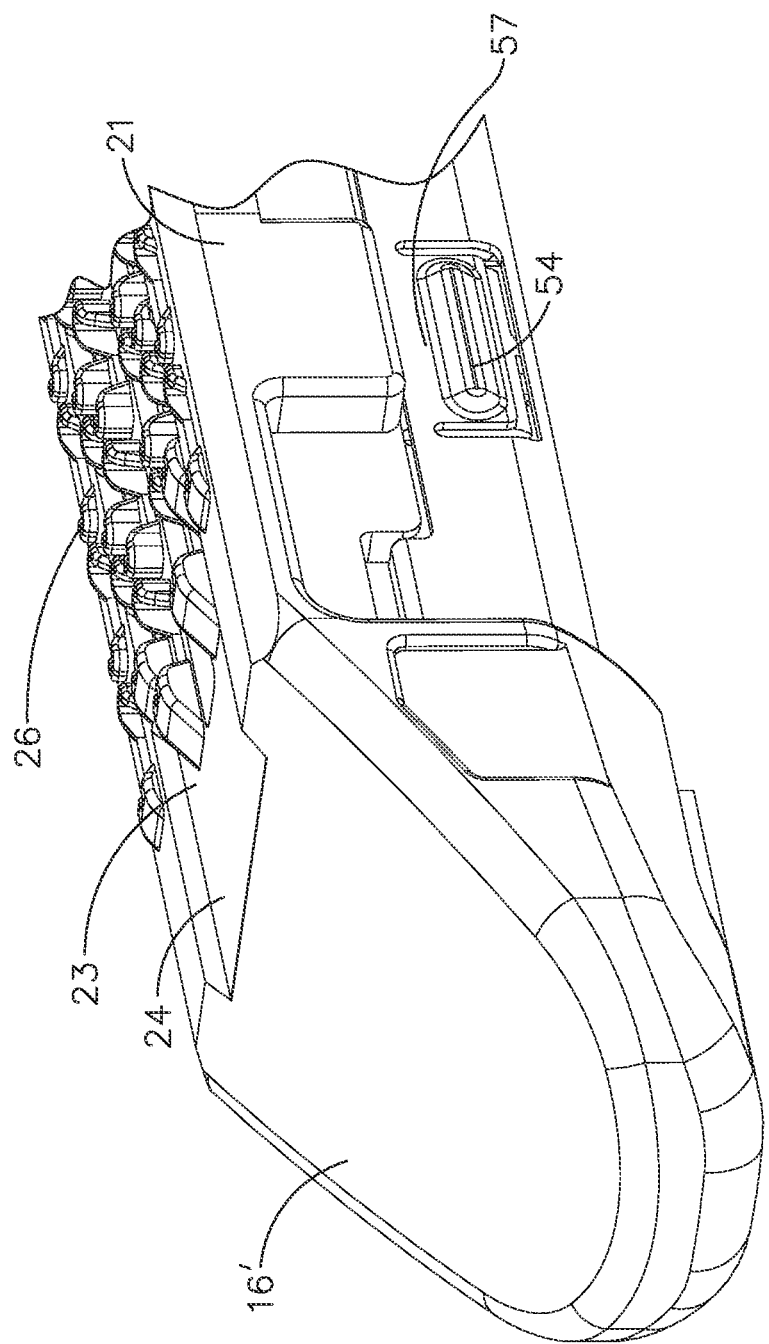
FIG. 13 illustrates a partial view of the staple cartridge of FIG. 12.
Figure 14:
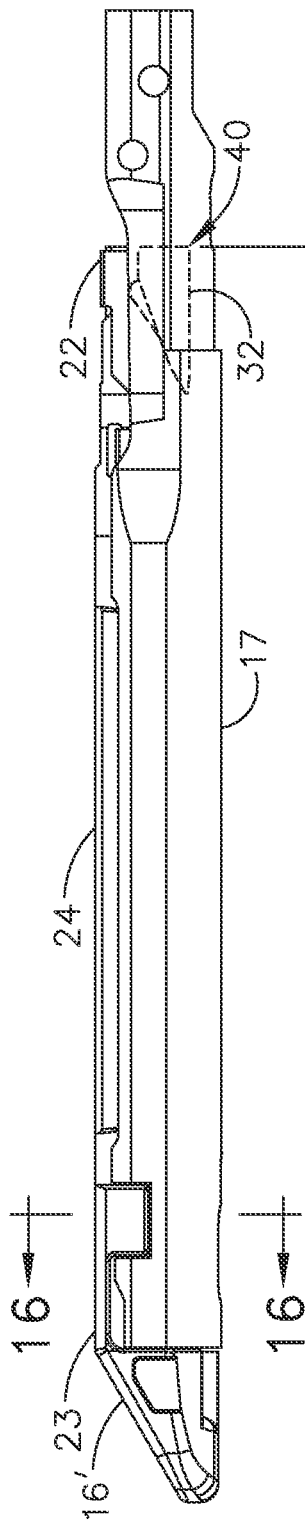
FIG. 14 illustrates a staple cartridge assembled with a cartridge channel of the surgical instrument of FIG. 1 with a sled shown in phantom lines in a proximal position.
Figure 15:
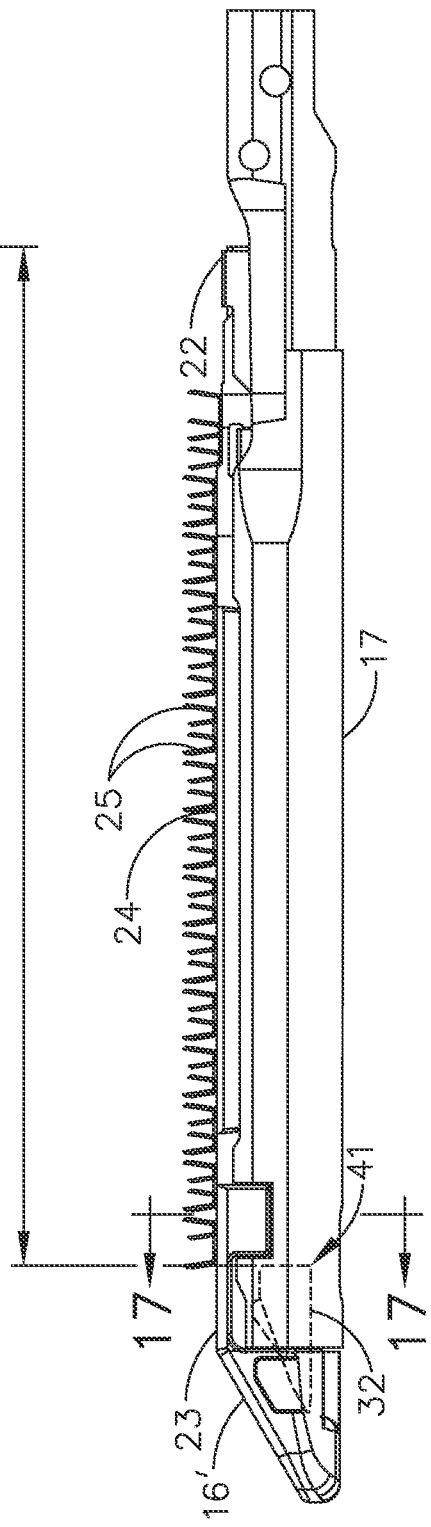
FIG. 15 illustrates a staple cartridge assembled with a cartridge channel of the surgical instrument of FIG. 1 with a sled shown in phantom lines in a distal position.
Figure 16:
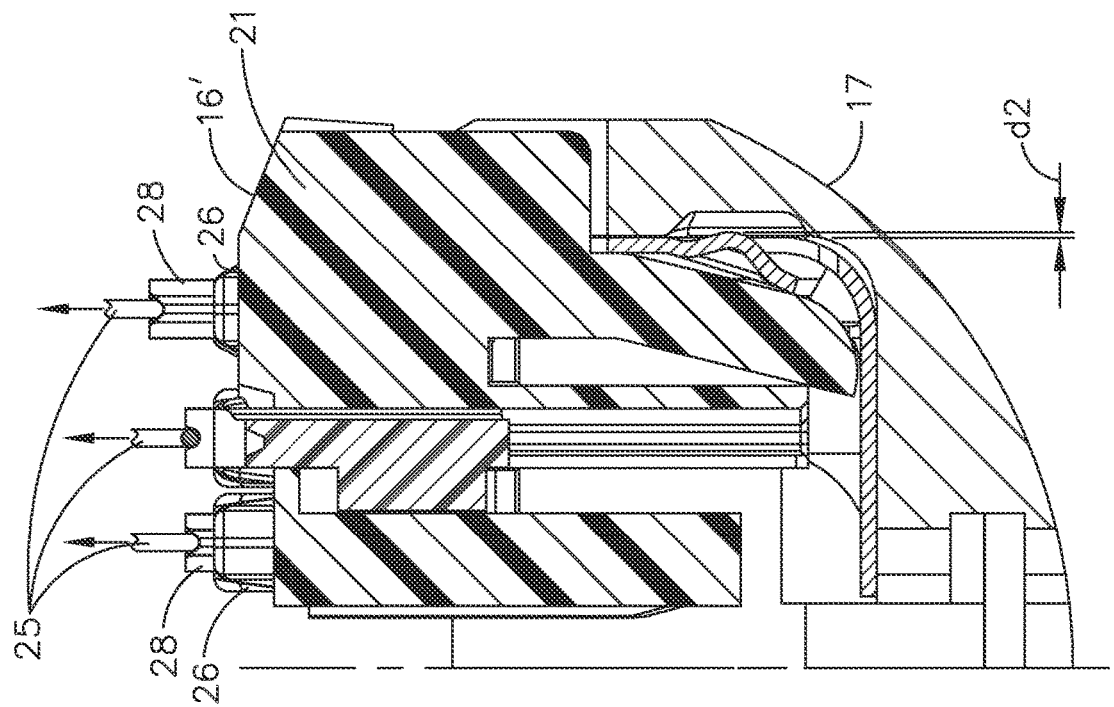
FIG. 16 illustrates a cross-sectional view taken along line 16-16 of FIG. 14.
Figure 17:
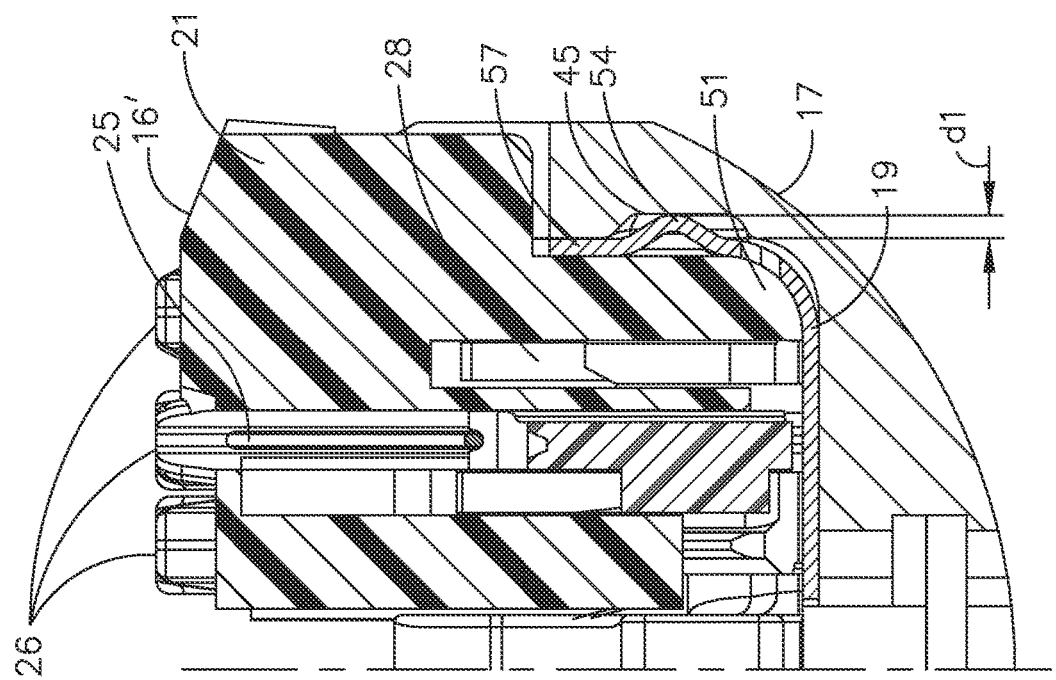
FIG. 17 illustrates a cross-sectional view taken along line 17-17 of FIG. 15.

In an alternative embodiment, as illustrated in the example of FIGS. 12-17, a staple cartridge 16', which is similar in many respects to the staple cartridge 16, can be removably seated in the cartridge channel 17. The staple cartridge 16', however, includes retaining members 57 that do not directly rest against the staple drivers 28 in the biased configuration. As best illustrated in FIGS. 16 and 17, the retaining members 57 are configured to rest, in the biased configuration, against a flexible portion 51 of the cartridge body 21 of the staple cartridge 16'. In other words, the staple drivers 28 of the staple cartridge 16' are not directly exposed to the retaining members 57 but, instead, are configured to provide support for the retaining members 57 through the flexible portion 51. In various examples, as illustrated in FIG. 12, the flexible portion 51 is formed by creating slits 61 in a side wall 62 of the cartridge body 21.

Like the staple cartridge 16, the staple cartridge 16' includes two retaining members 57 on opposite sides of the staple cartridge 16'. The retaining members 57 are configured to maintain, or to help maintain, a tight attachment between the staple cartridge 16' and the cartridge channel 17. Unlike the retaining members 37 of the staple cartridge 16, the retaining members 57 of the staple cartridge 16' do not extend from the base 19 of the retainer 30. On the contrary, the retaining members 57 are separated from the base 19 by a slit 58. Instead, the retaining members 57 extend toward the base 19, and can be formed creating slits 60 in walls 39 of the retainer 30 to permit the retaining members to flex relative to the walls 39.

Like the retaining members 37, each retaining member 57 includes a curved portion 54 that defines a retention feature or detent receivable in the depression or groove 45 defined in the side wall 46 of the cartridge channel 17. The curved portion 54 is retained in the groove 45 while the retaining member 57 is in the biased configuration to maintain, or to help maintain, a tight attachment between the staple cartridge 16' and the cartridge channel 17.

Prior to firing the staple cartridge 16' seated in the cartridge channel 17, as illustrated in FIG. 16, the retaining member 57 is biased an interference distance (d1) by the at least one staple driver 28 toward the side wall 46, which causes the curved portion 54 to be secured in the groove 45 yielding the pre-firing cartridge removal load.

During firing, however, the sled 32 is advanced by the firing member causing the at least one staple driver 28 to be lifted or moved out of engagement, or at least partially out of engagement, with the flexible portion 51. Consequently, as illustrated in FIG. 17, the flexible portion 51 flexes toward the space previously occupied by the at least one staple driver 28, which permits the retaining member 57 to return to the unbiased, or less biased, configuration, which causes the curved portion 54 to fall out of engagement, or at least partially out of engagement, with the groove 45 yielding the post-firing cartridge removal load. In the less biased configuration, as illustrated in FIG. 17, the retaining member 57 is biased an interference distance d2 from a natural position, the interference distance d2 being less than the interference distance d1.

In some examples, the curved portion 54 remains partially inserted in the groove 45 in the unbiased configuration. Consequently, the retaining member 57 contributes to the post-firing cartridge removal load. In other examples, however, the curved portion 54 may be fully removed from the groove 45 in the unbiased configuration. In the other examples, the retaining member 57 does not contribute to the post-firing cartridge removal load, which can be governed by the friction between the walls 39 of the staple cartridge 16 and the cartridge channel 17.

In the examples of FIGS. 4-17, the retaining members 37 and 57 are portrayed in a biased configuration while engaged with the groove 45, and in an unbiased, or less biased, configuration while disengage, or partially disengaged, from the groove 45. In other examples, however, retaining members of the staple cartridge can be configured to be in a natural or unbiased configuration while engaged with the groove 45. An external force can be applied, for example by the sled 32, to bias such retaining members out of engagement with corresponding groove 45 during firing of the staple cartridge.

In various examples, the post-firing cartridge removal load is about 10% to about 90% less than pre-firing cartridge removal load. In at least one example, the post-firing cartridge removal load is about 40% to about 60% less than pre-firing cartridge removal load. In at least one example, the post-firing cartridge removal load is about 50% less than pre-firing cartridge removal load.

In various aspects, a surgical instrument, similar in many respects to the surgical instrument 10, has a post-firing cartridge removal load higher than its pre-firing cartridge removal load. The higher post-firing removal load can prevent a spent, also referred to herein as fired, staple cartridge from being removed after firing, which effectively rendering the surgical instrument unusable.

Preventing a fired staple cartridge from being removed from a cartridge channel of the surgical instrument after firing can be advantageous in situations where reusing the surgical instrument after firing is undesirable. For example, the higher post-firing cartridge removal load of a surgical instrument, relative to its pre-firing cartridge removal load, can be in situation involving firing a non-sterile (e.g. endoscopic) staple cartridge. After firing the non-sterile staple cartridge with the surgical instrument, the surgical instrument becomes non-sterile as well. The higher post-firing cartridge removal load prevents the spent staple cartridge from being removed from the surgical instrument ensuring that the surgical instrument will not be reused.

In one example, the post-firing cartridge removal load can be increased to prevent removal of a spent staple cartridge by employing a locking feature that is retained in a biased configuration prior to firing a staple cartridge. During firing, the locking feature snaps into a locking engagement with the cartridge channel preventing removal of the spent staple cartridge from the cartridge channel. The cartridge channel may include a retaining window that receives the locking feature.

In one aspect, the staple drivers can be utilized to maintain the locking feature in its biased configuration. During firing of the staple cartridge, as the staple drivers are lifted by the sled, the locking feature is freed from its engagement with the staple drivers. The biasing force causes the locking feature to snap into locking engagement with the cartridge channel. More than one locking feature can be employed along the length of a staple cartridge to ensure that the spent staple cartridge remains attached to the cartridge channel.

In various examples, a higher post-firing cartridge removal load of a surgical instrument, relative to its pre-firing cartridge removal load, can be beneficial in ensuring that the surgical instrument will not be used beyond a predetermined number of firings. In at least one example, a firing assembly of the surgical instrument can be slightly advanced into the last fired staple cartridge preventing its removal from the surgical instrument. A controller of the surgical instrument can be configured to track the number of firings performed by the surgical instrument. Upon reaching a predetermined number of firings, the controller may activate a motor to slightly advance the firing assembly into the staple cartridge, which prevents removal of the last spent, or fired, staple cartridge to prevent the surgical instrument from being reused beyond its safe limits.

In another example, a higher post-firing cartridge removal load of a surgical instrument, relative to its pre-firing cartridge removal load, can be beneficial in permanently deactivating a defective surgical instrument. A controller of the surgical instrument can be configured to track various performance parameters of the surgical instrument. The controller may prevent the surgical instrument from being reused if the controller detects a defect in the surgical instrument. As described above, preventing the surgical instrument from being reused can be achieved by preventing removal of the last spent, or fired, staple cartridge. Suitable controllers, motors, and firing assemblies for use in preventing a spent, or fired, staple cartridge from being removed from the surgical instrument are disclosed in U.S. patent application Ser. No. 13/803,210, titled SENSOR ARRANGEMENTS FOR ABSOLUTE POSITIONING SYSTEM FOR SURGICAL INSTRUMENTS, and filed Mar. 14, 2013, now U.S. Pat. No. 9,808,244, which is hereby incorporated by reference herein in its entirety.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

EXAMPLES

Example 1-A surgical instrument that comprises a sled and an end effector. The end effector comprises a first jaw, a second jaw movable relative to the first jaw, an anvil, and a staple cartridge. The staple cartridge comprises a proximal end, a distal end, a cartridge body, a staple supported in the cartridge body, and a staple driver. The sled is configured to deploy the staple from the cartridge body by moving the staple driver from a first position to a second position. The end effector further comprises a cartridge channel configured to removably retain the staple cartridge. A first load is required to remove the staple cartridge from the cartridge channel while the staple driver is in the first position. A second load that is less than the first load is required to remove the staple cartridge from the cartridge channel while the staple driver is in the second position.

Example 2—The surgical instrument of Example 1, wherein the sled is movable between the proximal end and the distal end to deploy the staple.

Example 3—The surgical instrument of Example 2, wherein the first load is reduced to the second load during the movement of the sled toward the distal end.

Example 4—The surgical instrument of Example 1, 2, or 3 wherein the cartridge body comprises a window corresponding to the first position of the staple driver.

Example 5—The surgical instrument of Example 1, 2, 3, or 4, further comprising a retaining member configured to rest against the staple driver while the driver is in the first position.

Example 6—The surgical instrument of Example 5, wherein the retaining member is maintained in a biased configuration by the staple driver while the driver is in the first position.

Example 7—The surgical instrument of Example 5 or 6, wherein the retaining member is configured to return to a less biased configuration when the staple driver is moved to the second position.

Example 8—The surgical instrument of Example 5, 6, or 7, wherein the retaining member comprises a detent, and wherein the cartridge channel comprises a groove configured to receive the detent while the staple driver is in the first position.

Example 9—The surgical instrument of Example 8, wherein the detent is at least partially removed from the groove while the staple driver is in the second position.

Example 10—The surgical instrument of Example 8 or 9, wherein the detent is a first detent, and wherein the retaining member comprises a second detent supportable by the staple driver while the staple driver is in the first position.

Example 11-A staple cartridge removably attachable to a cartridge channel of a surgical instrument. The staple cartridge comprises a proximal end, a distal end, and a cartridge body. The cartridge body comprises a deck extending between the proximal end and the distal end, a staple deployable into tissue positioned against the deck, a staple driver movable between a first position and a second position to deploy the staple from the cartridge body, and a flexible portion positioned against the staple driver while the staple driver is in the first position. The staple cartridge further comprises a retainer attached to the cartridge body. The retainer comprises a resilient member positioned against the flexible portion. The flexible portion is configured to maintain the resilient member in a biased configuration while the staple driver is in the first position.

Example 12—The staple cartridge of Example 11, wherein the movement of the staple driver from the first position to the second position causes the flexible portion to flex, which causes the resilient member to return to a less biased configuration.

Example 13—The staple cartridge of Example 11 or 12, wherein the movement of the staple driver from the first position to the second position causes the flexible portion to flex, which causes the resilient member to return to a less biased configuration.

Example 14—The staple cartridge of Example 13, wherein the detent is configured to maintain a post-firing load for removing the cartridge from the cartridge channel in the less biased configuration, and wherein the post-firing load is less than the pre-firing load.

Example 15—The staple cartridge of Example 11, 12, 13, or 14, wherein the flexible portion is positioned between the staple driver and the resilient member while the staple driver is in the first position.

Example 16—The staple cartridge of Example 11, 12, 13, 14, or 15, wherein the retainer includes a base and a side wall extending from the base, wherein the resilient member is defined in the side wall, and wherein the resilient member is spaced apart from the base.

Example 17—The staple cartridge of Example 11, 12, 13, 14, 15, or 16, wherein the cartridge body further comprises a side wall, and wherein the flexible portion is defined in the side wall.

Example 18-A surgical instrument that comprises a sled and an end effector. The end effector comprises a first jaw, a second jaw movable relative to the first jaw, an anvil, and a staple cartridge. The staple cartridge comprises a proximal end, a distal end, a cartridge body, and staples supported in the cartridge body. The sled is movable to deploy the staples from the cartridge body against tissue captured between the staple cartridge and the anvil. The end effector further comprises a cartridge channel configured to removably retain the staple cartridge, wherein a load is required to remove the staple cartridge from the cartridge channel, and wherein the sled is configured to reduce the cartridge removal load.

Example 19—The surgical instrument of Example 18, wherein the sled is movable from a first position adjacent the proximal end to a second position adjacent the distal end to deploy the staples.

Example 20—The surgical instrument of Example 18 or 19, wherein the cartridge removal load is reduced during the movement of the sled.

What is claimed is:

1. A staple cartridge, comprising:
   a cartridge body comprising a cavity and a flexible portion;
   a staple supported in the cartridge body;
   a staple driver, wherein movement of the staple driver from a first position to a second position deploys the staple; and
   a tray attached to the cartridge body, the tray comprising:
      a base supporting the staple driver in the first position;
      a wall extending from the base; and
      a retainer maintained in a biased configuration by the flexible portion while the flexible portion is supported by the staple driver in the first position;
   wherein the retainer is released from the biased configuration when the flexible portion is unsupported by the staple driver in the second position.

2. The staple cartridge of claim 1, wherein when the flexible portion is supported by the staple driver in the first position the retainer is biased a first distance and when the flexible portion is unsupported by the staple driver in the second position the retainer is biased a second distance that is less than the first distance.

3. The staple cartridge of claim 2, wherein releasing the retainer from the biased configuration comprises permitting the retainer to move deeper into the cartridge body to a less biased configuration.

4. The staple cartridge of claim 3, wherein the retainer comprises a detent protruding away from the cartridge body and supportable by the flexible portion while the flexible portion is supported by the staple driver in the first position.

5. The staple cartridge of claim 1, wherein the wall comprises the retainer, and wherein the retainer is a cutout portion of the wall.

6. The staple cartridge of claim 5, wherein the cartridge body further comprises a side wall, and wherein the flexible portion is a cut out portion of the side wall.

7. The staple cartridge of claim 6, wherein the retainer is a first retainer, the wall is a first wall, the flexible portion is a first flexible portion, and the side wall is a first side wall, and wherein the tray further comprises a second wall and the cartridge body further comprises a second side wall, the second wall comprising a second retainer and the second side wall comprising a second flexible portion.

8. A staple cartridge, comprising:
   a cartridge body comprising a cavity and a flexible portion;
   a staple supported in the cartridge body;
   a staple driver, wherein movement of the staple driver from a first position to a second position deploys the staple; and
   a pan, comprising:
      a base supporting the staple driver in the first position;
      a wall extending from the base; and
      a tab defined by a cutout portion of the wall extending toward the base,
   wherein the tab is maintained in a first biased configuration by the flexible portion while the flexible portion is maintained in a second biased configuration by the staple driver in the first position; and
   wherein the tab is released from the first biased configuration when the flexible portion is released from the second biased configuration by the staple driver in the second position.

9. The staple cartridge of claim 8, wherein the cutout portion of the wall separates the tab from the base.

10. The staple cartridge of claim 8, wherein the cartridge body further comprises a side wall, and wherein the flexible portion is a cut out portion of the side wall.

11. The staple cartridge of claim 10, wherein the tab is a first tab, the wall is a first wall, the flexible portion is a first flexible portion, and the side wall is a first side wall, and wherein the pan further comprises a second wall and the cartridge body further comprises a second side wall, the second wall comprising a second tab and the second side wall comprising a second flexible portion.

12. The staple cartridge of claim 8, wherein the tab is movable relative to the wall toward and away from the cartridge body.

13. The staple cartridge of claim 12, wherein releasing the tab from the first biased configuration comprises permitting the tab to move deeper into the cartridge body to a less first biased configuration.

14. The staple cartridge of claim 13, wherein the tab comprises a detent protruding away from the cartridge body and supportable by the flexible portion while the flexible portion is in the second biased configuration.

15. A surgical instrument, comprising:
an end effector comprising a cartridge channel; and
a staple cartridge removably insertable into the cartridge channel, the staple cartridge comprising:
 a cartridge body comprising a cavity and a flexible portion;
 a staple supported in the cartridge body;
 a staple driver, wherein movement of the staple driver from a first position to a second position deploys the staple; and
 a pan, comprising:
  a base supporting the staple driver in the first position; and
  a retainer maintained in a biased configuration by the flexible portion while the flexible portion is supported by the staple driver in the first position;
  wherein the retainer is released from the biased configuration when the flexible portion is unsupported by the staple driver in the second position.

16. The surgical instrument of claim 15, wherein the staple cartridge is removably maintained in the cartridge channel of the end effector by the retainer while in the biased configuration.

17. The surgical instrument of claim 16, wherein a first load is required to remove the staple cartridge from the cartridge channel while the staple driver is in the first position, and wherein a second load less than the first load is required to remove the staple cartridge from the cartridge channel while the staple driver is in the second position.

18. The surgical instrument of claim 15, wherein the retainer is a first retainer and the flexible portion is a first flexible portion, and wherein the pan comprises a second retainer spaced apart from the first retainer and the cartridge body comprises a second flexible portion spaced apart from the first flexible portion.

19. The surgical instrument of claim 15, wherein the retainer comprises a detent protruding away from the cartridge body and supportable by the flexible portion while the flexible portion is supported by the staple driver in the first position.

20. The surgical instrument of claim 19, the cartridge channel comprises a groove configured to receive the detent while the flexible portion is supported by the staple driver in the first position, and wherein the detent is at least partially removed from the groove while the flexible portion is unsupported by the staple driver in the second position.

* * * * *